Figure 1:
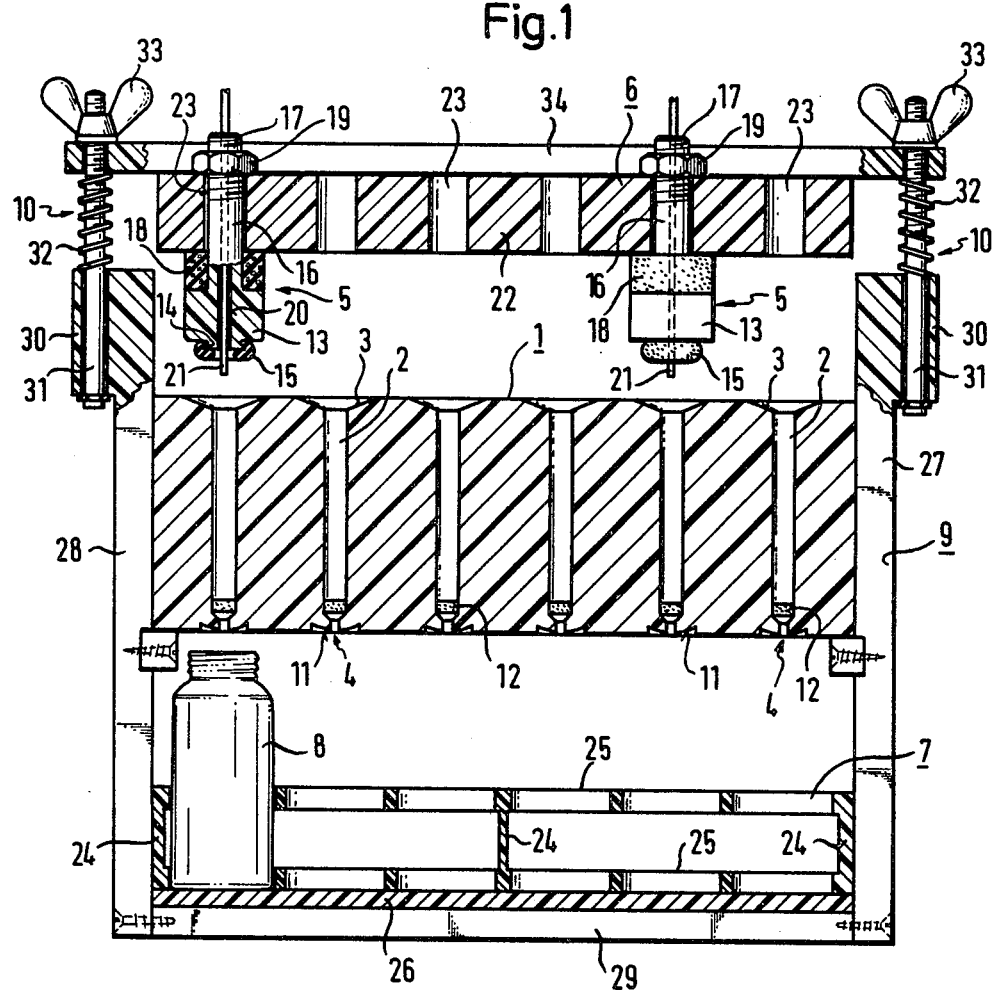

United States Patent [19]

Seiler et al.

[11] 4,079,009
[45] Mar. 14, 1978

[54] APPARATUS FOR MULTIPLE COLUMN CHROMATOGRAPHY

[75] Inventors: Nikolaus Seiler, Frankfurt am Main; Bernd Knödgen, Langen; Wilhelm Seyl, Frankfurt am Main, all of Germany

[73] Assignee: Max-Planck-Gesellschaft zur Foerderung der Wissenschaften, e.V., Goettingen, Germany

[21] Appl. No.: 731,310

[22] Filed: Oct. 12, 1976

[30] Foreign Application Priority Data

Oct. 14, 1975 Germany .............................. 2545997

[51] Int. Cl.² ............................................ B01D 15/08
[52] U.S. Cl. .................................... 210/198 C; 55/386
[58] Field of Search ............. 210/31 C, 198 C; 55/67, 55/386

[56] References Cited

U.S. PATENT DOCUMENTS

| | | | |
|---|---|---|---|
| 2,960,183 | 11/1960 | Kelly | 55/386 X |
| 3,922,223 | 11/1975 | Burkhartsmeier | 55/386 X |

*Primary Examiner*—John Adee
*Attorney, Agent, or Firm*—Hans Berman

[57] ABSTRACT

Upright bores in a unitary plastic block are connected by respective hoses and column heads to a multiple-tube peristaltic pump for simultaneous supply of liquid to be chromatographed on ion exchange resin in the bores. The hoses are attached to a common carrier for the several heads and sealed to the columns by pressing the carrier toward the block. The columns are eluted simultaneously by pumped liquid, and the eluates are collected in vessels on a common support.

11 Claims, 2 Drawing Figures

APPARATUS FOR MULTIPLE COLUMN CHROMATOGRAPHY

The invention relates to apparatus for multiple column chromatography, that is, to apparatus in which a multiplicity of specimens can be subjected to chromatography simultaneously and independently from each other in separate columns.

Heretofore, individual tubes or columns were employed in column chromatography and were loaded with a solid carrier, charged with the specimen to be chromatographed, and thereafter rinsed with an eluent. These columns, mostly made of glass, must be fastened individually by the user to stands or frames and connected to a pump by respective hose connections if the specimen and the eluent are not charged manually.

The conventional columns thus require a substantial expenditure of manual labor, particularly when a large number of specimens is to be chromatographed. Because of this expenditures of labor, the number of specimens to be analyzed within a practical period was mostly restricted. There is a need, therefore, for an apparatus by means of which a great number of specimens can be chromatographed simultaneously under uniform conditions without requiring the handling of a multiplicity of individual chromatographic columns.

The object of the invention, then, resides in the provision of apparatus for multiple column chromatography which permits economical multiple column chromatography on a routine basis and reduces the expenditure of labor necessary heretofore.

The invention thus provides apparatus for multiple column chromatography characterized by a column block in which a multiplicity of columns are formed integrally as elongated, cylindrical through-passage having a column intake at the top of the block and a column outlet at the underside;
column heads respectively connectable with the several
 column intakes spatially arranged for supplying the material to be chromatographed and the eluent;
a column head carrier for receiving the column heads arranged in accordance with the columns;
a support for the receiving vessels; and
a stand equipped with a pressing device permitting all column heads to be pressed firmly and simultaneously against the column intakes, for receiving the column head carrier, the column block, and the support for the receiving vessels.

The column intakes are preferably conical so that tightly connecting the column intakes to the column heads is facilitated.

The column outlets may have the same diameters as the columns or may include convexly shaped draining faces integrally formed in the column block, the columns tapering toward the outlets and terminating in the centers of the draining faces. The tapering column ends are preferably closed by a porous material retaining the sorptive agent but permeable to liquid. Glass wool or plastic wool or a fritted body of glass, ceramic, or plastic is employed, preferably fritted polyethylene or other fritted, corrosion resistant material.

The column block which defines the multiplicity of columns preferably consists of plastic, such as polyethylene, polyvinyl chloride, or the like in which the columns are formed integrally by drilling, by injection molding of the entire block, or in a similar manner. The column block may comprise any number of columns which may all be operated simultaneously if so desired. However, it is also possible to use only a certain number of available columns.

The column heads sealingly connectable to the column intakes and spatially arranged in the column head carrier to match the column intakes preferably include a cylindrical lower portion having an annular groove for receiving a sealing ring of rubber, plastic, Teflon, or the like, and a cylindrical upper portion whose diameter is smaller than that of the lower portion. The top end of the upper portion has threads so that the column head may be fastened to the column head carrier by means of a nut, a resilient material, for example cellular plastic or foam rubber, being preferably arranged between the lower portion of the column head and the column head carrier to compensate for non-planar surfaces and in order to facilitate a resilient, tight connection between the column head and the columns. The column heads have each an axial bore through which a tightly fitting hose of rubber or plastic, preferably Teflon, is passed for charging the column with the specimen and for supplying the eluent. This hose is connected to a multiple-tube peristaltic pump by means of which the several columns are supplied with the same or different specimens or eluents. Because of the tight connection of the columns to the pump achieved in this manner, a flow pattern uniform within the limits of uniformity of the pumping process is enforced, a significant advantage over manually performed column separations by means of individual columns, because substantially cleaner separations can be achieved in this manner.

The column heads are made of non-corroding material, for example of plastic, and are fastened to the column head carrier consisting of a plate provided with a row of bores which correspond in number and arrangement to the columns or the column heads. The upper portions of the column heads are inserted in the bores and fixed by means of threads and nuts. The plate, and thereby all the column heads, are pressed firmly against the column block and thus against the column intakes by means of a pressing device, whereby a tight seal between the column heads and the columns is achieved. The pressing device includes threaded spindles fastened to the stand which receives the column head carrier, the column block, and the support for the receiving vessels, and springs and wing nuts slipped over the spindles by means of which the column head carrier with the column heads is pressed against the column block.

Further embodiments, objects, and advantages of the invention will be evident from the following description referring to the drawings.

Figure 2:
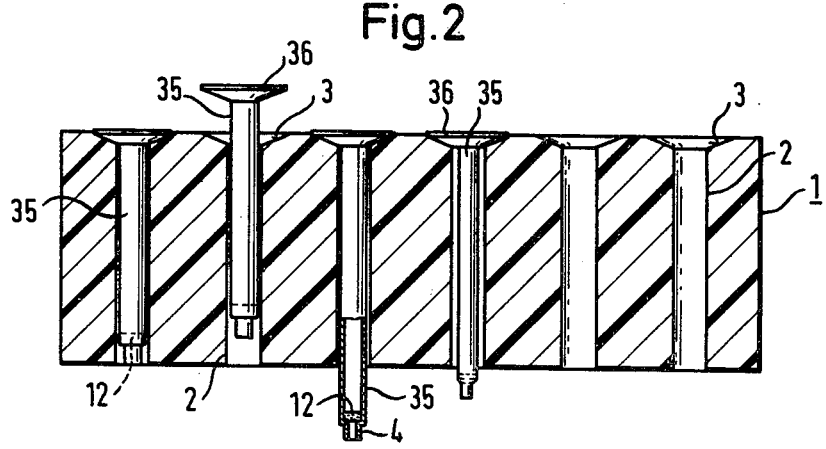

FIG. 1 shows a sectional side elevation of the multiple column chromatography apparatus of the invention, whereas FIG. 2 represents an additional embodiment of the column block according to the invention.

As is seen in FIG. 1, the apparatus for multiple column chromatography according to the invention includes a column block 1 of plastic or similar material in which a multiplicity of cylindrical columns 2 is integrally formed, each column having a conical column intake 3 at the top of the block and a column outlet 4 at the underside. The column outlets 4 have each a convexly shaped drainage face 11 recessed in the column block 1, the column tapering toward the outlet and terminating in the center of the face 11. The column ends are closed by means of a liquid permeable, porous material 12, for example a body of fritted glass, ceramic material, or plastic, preferably polyethylene. This porous material 12 is permeable to liquids, but retains the solid filler material in the columns 2. The column block 1 consists of a corrosion resistant material stable in the presence of the eluents used, for example plastic such as polyetheylene, polyvinyl chloride, Teflon, or the like. The columns 2 are integrally formed in the column block, for example by drilling. However, the column block may also be produced by injection molding, casting, or the like.

The column heads 5 are fastened to the column head carrier 6, located above the column block 1, in such a manner that their arrangement corresponds to the column intakes 3 of the columns 2 in the column block 1. The column head carrier 6 includes a plate 22 consisting, for example, of plastic, and is provided with a multiplicity of bores 23 whose internal diameter corresponds to the diameter of the upper portions 16 of the column heads 5. These bores are arranged in the same manner as the columns 2 in the column block 1.

The column heads 5 fastened in the column head carrier 6 have each a cylindrical lower portion 13. This lower portion 13 is provided with an annular groove 14 for receiving a sealing ring 15 of rubber, plastic, or the like. The cylindrical upper portion 16 of the column head 5, longer by comparison to the lower portion, has a smaller diameter and is provided at its top end with threads 17. The thinner upper portions 16 of the column heads 5 are inserted into the bores 23 of the column head carrier 6 and fixed by means of the nut 19 and the threads 17. A resilient material 18, for example foam rubber sponge, which is arranged between the wider lower portion 13 of the column head 5 and the column head carrier 6 enhances the resilient pressing of the column heads 5 toward the column intakes 3. A tightly fitting hose 21 of rubber, plastic, and preferably Teflon, is inserted in the bore 20 of each column head 5. The specimens are charged, and the eluent is supplied through these hoses. The individual hoses 21 of the several column heads 5 are connected to a multiple-tube peristaltic pump (not illustrated) which conveys the specimens and the eluent. The column heads 5 may also be made of plastic.

The column block 1 as well as the support 7 for the receiving vessels 8 are provided in a stand 9 to which the column head carrier 6 is also fastened by means of the pressing device 10. The stand 9 is preferably made of plastic and includes wide walls 27, 28, a bottom 29 and attachments 30 for the pressing device 10. The pressing device 10 to which the column head carrier 6 is fastened, includes threaded spindles 31 anchored in the attachments 30 of the stand 9, springs 32, wing nuts 33, and a pressing plate 34. The pressing plate 34 and thereby the column head carrier 6 are pressed against the column block 1 by tightening the wing nuts 33, whereby by means of the sealing ring 15, preferably a Viton seal, a tight connection between the column heads 5 and the column intakes 3 or the columns 2 is achieved. The support 7 for the receiving vessels 8 arranged below respective column outlets 4 is located below the column block 1. The support has side- and center walls 24, plates 25 with openings for the receiving vessels 8, and a continuous bottom 26. The support 7 also is preferably made of plastic, for example, polyethylene or polyvinyl chloride.

For use of the apparatus according to the invention, the columns 2 whose ends are closed by the porous material 2 are filled with a filler material, for example pulverulent, whereupon the specimens may be charged by hand, if desired. Thereafter, the column block 1 is installed in the stand 9 whereupon the column heads 5 are pressed tightly on the column intakes 3 by tightening the pressing device 10. After insertion of the support 7 with the receiving vessels 8, the specimens are charged to the columns 2 by way of the hoses 21, if not supplied earlier. The eluent or eluents then are pumped by means of the non-illustrated multiple-tube peristaltic pump through the hoses 21 into the columns causing a very uniform chromatographic process. Chromatographic separation then is performed by the charged columns in the usual manner, the receiving vessels 8 being replaced as needed for receiving the desired fractions.

After separation, the pressing device 10 is released and the column block 1 is withdrawn. Because of the arrangement of the columns in the form of a block, filling, emptying, and cleaning and general handling are substantially simplified as compared to the known application of individual columns.

As is seen in FIG. 2, the column block 1 may also be provided with columns 2 having, instead of a tapering outlet 4, a uniformly cylindrical column which does not taper at its outlet end 4. Tubular, individual columns 35 may be inserted into these columns 2 whose intakes are conical in shape, the columns 35 having each a funnel-shaped end 36 at its top, and which may be of different lengths and/or diameters. It is possible by means of this block to use in one block columns of different lengths and, within certain limits, also columns of different diameters. The tubular columns 35 taper at the column outlets 4 and are preferably closed there by means of porous material 12, for example a fritted body of glass, ceramic, plastic, preferably polyethylene. In this event, pre-packed tubular columns 35 may also be employed.

In a test for uniformity of elution and for reproducibility of consecutive chromatographic separations, radioactive compositions were separated chromatographically by means of a multiple column chromatography apparatus of the invention having 48 columns. It was found that all 48 columns behaved in the same manner, and reproducible results were achieved.

Furthermore, a method for determining monoaminoxidase (using radioactive amines as substrates), which had been developed in individual glass columns, was tested in the apparatus according to the invention. Reproducibility are reliability of the test series were the same in both cases.

The multiple column chromatography apparatus of the invention is particularly suited for routine determination of enzymes by means of radioactive compounds, for the chromatographic separation, purification, and concentration of certain substances in numerous specimens (for example for subsequent quantitative determination), and also for radioimmuno assay.

The operation of the apparatus according to the invention is illustrated by the following:

EXAMPLE

Determination of Monoaminoxidase (MAO) Activity in Blood Platelets.

Basis of the Method:

Blood platelets recovered from whole blood by differential centrifuging are incubated in phosphate buffer at pH 7.4 and 37° C with a labeled amine ($^{14}C$ serotonin, $^{14}C$-$\beta$-phenylethylamine; $^{14}C$-tryptamine, etc.). A portion of the amines reacts according to the following reaction in which an aldehyde is formed:

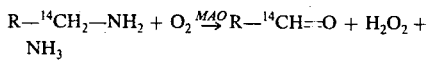

The aldehyde formed in this reaction may further react partially or entirely with an aldehyde-dehydrogenase to form the corresponding acid:

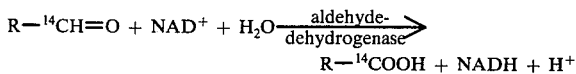

The amount labeled aldehyde and/or acid (that is, the sum of these reaction products) formed in a unit of time under standardized conditions is a measure of the activity of the MAO in the reaction mixture and, under certain conditions, also a measure of the amount of enzyme.

The goal of the method is the determination of the sum of aldehyde and acid. A simple procedure consists in separating the excess of radioactive amine still present in the reaction mixture by means of a cation exchanging material from the aldehyde and the acid, and to measure the radioactivity in the aldehyde + acid fraction (not retained by the cation exchange material).

Application of the Apparatus for Multiple Column Chromatography: Introductory Note; The testing of numerous specimens (for example, from patients showing certain symptoms of disease) is necessary for certain reasons. It is also necessary to process the recovered blood platelets as quickly as possible because their properties change in storage.

For each apparatus (column head carrier 6 with column heads 5, stand 9 with pressing device 10), several column blocks 1 and supports 7 for the receiving vessels should be available to permit optimum utilization of the capability of multiple column chromatography.

Carrying Out the Determination: The columns of about 1 ml capacity integrally formed in the column blocks are each filled with an aqueous suspension of a cation exchange resin (for example, Dowex 50W×8) up to the conical inlet opening, the water being permitted to drip through the porous fritted body 12 and the column outlet 4.

A resin-filled column block is inserted into the pressing device. The connection to a multiple-tube peristaltic pump is established by pressing the column heads 5. The seal between column and column head is provided by the sealing ring 15, a connection to the pump by means of a Teflon hose 21. A support 7 with receiving vessels 8 (suitable for liquid scintillation measurement) is also inserted in the stand.

The specimens are prepared for the determination of MAO in blood platelets in a conventional manner, not described here in detail. Suitable specimen preparing devices which permit rapid pipetting of the individual reactants and thus an economical mode of operation are available. The specimens assembled in suitable holders are incubated in a water bath. The enzyme reaction is interrupted at the end of the incubation period (for example, after 30 minutes) by adding 1 ml methanol (to 0.5 ml of reaction solution). Then, the specimens are placed below the suction part of the peristaltic pump, and the hollow needles which are arranged at the suction side of the pump in a suitable geometric relationship to the specimens in the holders are dipped into the specimens. The multiple-tube peristaltic pump is started at a pumping rate of 3 ml/hr. It conveys the contents of the specimen containers at a constant rate to the columns integrally formed in the column block and filled with ion exchange resin. After the contents of the reaction vessels are pumped to the columns, the vessels are each charged with 2 × 1 ml of a methanol/water mixture (3:1), and this liquid is pumped to the columns in the same manner as the reaction solution.

The eluent flowing out of the columns is employed directly for measuring radioactivity. Radioactivity is determined by measuring scintillation in a $\beta$-spectrometer after mixing of the column eluates with 10 ml of a liquid scintillator.

The column block is released by relaxing the pressing device (releasing the wing nuts 33). It is withdrawn from the holding stand and replaced by a block filled with fresh resin. After a new support 7 with receiving vessels 8 is inserted in the apparatus, separation of additional 48 specimens may begin.

Theoretically, the ion exchange resin may be regenerated by means of the apparatus described by adding pumped regenerating liquids (sodium hydroxide — water — hydrochloric acid — water). In practical application of the apparatus, it has been found that the columns integrally formed in the column blocks are easily emptied and washed by means of a weak jet of water introduced from the outlet end. Filling the columns with carrier material is equally easy, so that it is not normally worthwhile to regenerate the resin in the column block. It is more advantageous, for example, to regenerate the entire used resin at once at the end of a working day, and to fill several column blocks (or prepared columns) and to stock the same.

The procedure permits approximately 150 MAO determinations to be carried out within one working day by a technician.

We claim:

1. Apparatus for multiple column chromatography comprising:
   (a) a stand;
   (b) a column block on said stand,
      (1) said block having a top surface and an underside and being formed with a plurality of elongated passages therethrough between respective intake openings in said top surface and respective outlet openings in said underside;
   (c) a column head carrier secured to said stand;
   (d) a plurality of tubular column heads respectively associated with said intake openings and mounted on said carrier for joint movement therewith;
   (e) pressing means on said stand for moving said carrier and the column heads mounted thereon into a position in which said column heads sealingly engage the associated intake openings;
   (f) supply means for supplying liquid to said column heads; and
   (g) a support mounted on said stand below said outlet openings for supporting receiving vessels for liquid discharged from said outlet openings respectively.

2. Apparatus according to claim 1, wherein said passages are cylindrical, and said outlet openings have the same diameter as said passages.

3. Apparatus according to claim 1, wherein said passages are cylindrical and of greater diameter than the respective outlet openings.

4. Apparatus according to claim 1, wherein said underside is formed with a plurality of convexly shaped draining faces, the center of each draining face being formed with a respective one of said outlet openings.

5. Apparatus according to claim 4, wherein each of said passages tapers toward the associated outlet opening.

6. Apparatus according to claim 1, wherein each column head has two coaxial, axially offset portions of different diameter, the portion of smaller diameter being secured resiliently and threadedly to said carrier, and the portion of greater diameter carrying sealing means for connection with the associated intake opening.

7. Apparatus according to claim 6, wherein said carrier is formed with a plurality of bores matingly receiving respective ones of said portions of smaller diameter.

8. Apparatus according to claim 1, wherein said support has a continuous bottom wall and a plate member apertured for insertion of said receiving vessels between said bottom wall and said outlet openings.

9. Apparatus according to claim 1, wherein said pressing means include a plurality of threaded spindles secured to said stand, a plate member movably mounted on said spindles and abuttingly engaging said carrier, and nut means threadedly mounted on said spindles and engaging said plate member.

10. Apparatus according to claim 9, wherein said pressing means further include a plurality of springs operatively interposed between said stand and said plate member for biasing said plate member away from said intake openings.

11. Apparatus according to claim 1, further comprising a solid adsorbent in each of said passages.

* * * * *